United States Patent [19]

Buddell et al.

[11] Patent Number: 4,599,480

[45] Date of Patent: Jul. 8, 1986

[54] SEQUENTIAL CRACKING OF HYDROCARBONS

[75] Inventors: Robin L. Buddell, Kenner; Audrey M. Oswald, Destrehan; William A. Lagarde, Norco, all of La.

[73] Assignee: Shell Oil Company, Houston, Tex.

[21] Appl. No.: 755,035

[22] Filed: Jul. 12, 1985

[51] Int. Cl.$^4$ ................................................ C07C 4/02
[52] U.S. Cl. ................................ 585/650; 208/106; 208/107; 208/132; 585/654
[58] Field of Search ............... 208/106, 107, 132, 126, 208/48 AA; 585/650, 651, 648, 654

[56] References Cited

U.S. PATENT DOCUMENTS

| | | | |
|---|---|---|---|
| 2,111,900 | 3/1938 | Nagel | 585/650 |
| 3,617,478 | 11/1971 | King et al. | 585/650 |
| 3,827,967 | 8/1974 | Nap et al. | 208/106 |
| 4,259,177 | 3/1981 | Ueda et al. | 585/650 |
| 4,271,008 | 6/1981 | Vogt et al. | 208/48 R |
| 4,507,196 | 3/1985 | Reed et al. | 208/48 AA |
| 4,552,643 | 12/1985 | Porter et al. | 585/950 |

FOREIGN PATENT DOCUMENTS

| | | | |
|---|---|---|---|
| 232379 | 7/1959 | Australia | 585/654 |
| 243040 | 10/1960 | Australia | 585/650 |

OTHER PUBLICATIONS

R. T. K. Baker & D. J. C. Yates, "Filamentous Carbon Formation over Iron Surfaces", 1982 American Chemical Society.

L. F. Albright & R. T. K. Baker, "Coke Formation on Metal Surfaces", Aug. 27, 1981.

D. E. Brown, J. T. K. Clark, A. I. Foster, J. J. McCarroll & M. L. Sims "Inhibition of Coke Formation in Ethylene Steam Cracking", 1982.

A. I. Lacava, E. D. Fernandez-Raone & M. Caraballo, "Mechanism of Surface Carbon Formation During the Pyrolysis of Benzene in the Presence of Hydrogen", 1982, American Chemical Society.

A. I. Lacava, E. D. Fernandez-Raone, L. L. Issacs & M. Caraballo, "Effect of Hydrogen on the Iron- and Nickel-Catalyzed Formation of Carbon from Benzene", 1982, American Chemical Society.

M. J. Bennett & J. B. Price, "Oxidation of an Ethylene Steam Cracker Pyrolysis Tube Deposit in Water Vapor and its Enhancement by Inorganic Catalysts", 1982, American Chemical Society.

J. C. Marek & L. F. Albright, "Formation and Removal of Coke Deposited on Stainless Steel and Vycor Surfaces from Acetylene and Ethylene", 1982, American Chemical Society.

A. Sacco & J. C. Caulmare, "Growth and Initiation Mechanism of Filamentous Coke", 1982, American Chemical Society.

A. M. Brown & M. P. Hill, "The Characterization of Carbon Deposit Morphologies Using In Situ Scanning Electron Microscopy", 1982, American Chemical Society.

*Primary Examiner*—Andrew H. Metz
*Assistant Examiner*—A. Pal
*Attorney, Agent, or Firm*—Kimbley L. Muller

[57] ABSTRACT

In this process ethylene is prepared by pyrolytically cracking ethane in a pyrolytic cracking furnace having a plurality of elongated serpentine-situated thermal cracking tubes which have a longer run life as a result of the selective cracking of a $C_3$ to $C_{12}$ hydrocarbonaceous material at conditions sufficient to selectively place a coat of amorphous relatively smooth coat of coke on the interior walls of the thermal cracking tubes and thereby mask the catalytic effect of iron, nickel, both iron and nickel, or other metal catalytic sites indigenous to the walls of the furnished tubes. In this manner, the amount of cracking time realized for each particular furnace before regeneration of the same is increased by 20 to 50%.

37 Claims, 6 Drawing Figures

SEQUENTIAL CRACKING OF HYDROCARBONS

BACKGROUND OF THE INVENTION

The use of pyrolytic furnace tubes to crack ethane or other higher number carbon atoms to either ethylene or other hydrocarbonaceous materials has been practiced for at least fifty years. While other methods for producing ethylene are existent in the prior art, this application concerns only the pyrolytic or thermal cracking of ethane.

In 1981, the American Chemical Society conducted a symposium in regard to coke formation on metal surfaces. Some of the presented papers include those of Chapters 1, 2, 4, 5, 6, 7, 9, and 10. In Chapter 1 of that Symposium, Baker and Yates discussed filamentous carbon formation over iron surfaces. Cognizance was taken of the catalytic activity of iron oxide metal on the ethane cracking process at 700° C. In fact, disclosure is made that the pre-treatment of the iron surfaces with steam at 700° C. shows a dramatic increase in the catalytic cracking activity resulting in carbon deposition derivative of the applicable hydrocarbons. This is believed to be the result of the additional formation of FeO compounds. Steam treatment at 800° C. interacts with not only the uppermost layer of the iron in the pyrolytic reaction tubes but also penetrates an appreciable depth after a period of treatment of about three hours. In either event, the FeO compounds in the iron metal were found to have an extremely high activity with a formation of filamentous deposits of carbon compounds on the surface of iron metal surfaces. This type of coke formation leads to a tube wall metal attrition. It was at least theorized that the reason for high FeO activity is that same is a precursor for a high surface area iron catalyst formed in situ.

In Chapter 2, Brown et al recognize inhibition of coke formation in ethylene steam cracking, i.e. the quantity of coke deposition occurring in the coils and associated downstream heat exchangers can be mitigated, by coating the process vessel walls with a chemical vapor deposition of an alkoxysilane in a steam carrier gas to produce a thin impervious adherent amorphous silica film on the internal surfaces of the steel alloy. From the experimentation performed in regard to that paper, under certain conditions of temperature, steam, concentration, and flow rate, coke formation was found to be not rendered nugatory but was considerably reduced as a derivative of the silica coating.

Chapters 5 and 6 discuss the kinetics and mechanisms for the carbon formation as a result of the pyrolysis of benzene in the presence of hydrogen. Chapters 4, 7, 9, and 10 discuss growth initiation and morphologies of coke deposited on furnace tube walls.

FIELD OF THE INVENTION

This invention concerns a thermal cracking process to pyrolyze a paraffinic hydrocarbon to its olefinic counterpart. The most direct conversion is that of ethane to ethylene; with ethane producing the highest yield of ethylene per pound hydrocarbon feed basis. The pyrolysis of these hydrocarbons, and especially ethane, is highly endothermic in nature which requires use of a radiant furnace or fire box to provide sensible heat of reaction.

It is commonplace to subject ethane to traversal of a multitude of serpentine arranged elongated steel tubes in which the cracking of the ethane takes place to quickly to form ethylene. A number of major companies such as the Lummus Company, M. W. Kellogg Company, the Foster Wheeler Corporation, etc. make various types of pyrolytic fired heaters for commercial installation. Regardless of specific design, all these units are of a relatively fungible nature at least as concerns conversion rates.

Again, the preferred olefinic material prepared in these fired-heated furnaces is ethylene, which is one of the most important petrochemicals produced in industry today. While ethylene can be produced from propane, naphtha, hexane, etc. via pyrolytic cracking, ethane thermal cracking is generally the most beneficial route to acquire the desired ethylene. It is common knowledge that ethylene is one of the key fundamental building blocks of other organic compounds used in such areas as medicine, textiles, synthetic rubber, polymer production, etc.

In the thermal cracking of paraffinic material to olefinic material a certain amount of coke will be produced. It is inevitable that eventually this coke formation will deposit on the serpentine elongated tubular pyrolysis tubes and in any type of downstream heat exchange quench unit situated to accommodate treatment of the effluent from the pyrolytic cracking unit. The thermal cracking operation can withstand a certain amount of coke in the unit and still function in a viable manner. However, it is inevitable that coke will eventually build to such a level that clotting begins in the downstream cooling unit and part of the carbon deposit begin to flake off from the inner part of the pyrolytic reaction tubes causing spalled coke which necessitates furnace shutdown and removal of the coke. Once this phenomena occurs it is necessary to regenerate the furnace to its near virgin state by removing coke from the interior of the tube walls and heat exchanger by contact with a regeneration agent such as steam. This procedure is not only very expensive but it also results in attrition vis-a-vis the pyrolytic reaction furnace tubes shortening the life span for the tubes and the furnace. In addition, tube walls are thinned due to metal attrition occurring during filamentous coke formation. As a total renovation of these tubes is extremely expensive it is most desirable to produce the greatest amount of ethylene possible via pyrolytic cracking of ethane over the life of the tubes.

The temperature differential in the tops and bottoms of these serpentine-situated tubes is of great variance particularly during steam regeneration and acts to bow the tubes creating an even greater demand for the continued strength of the tube walls. It is a desire of most ethylene manufacturers, beginning with an ethane reactant, to achieve the longest run periods possible before shutdown and regeneration. The development of this process will provide such an opportunity for increased run lengths of from 20 to 50% greater vis-a-vis a furnace with only adaptability to the gaseous feed product. This invention requires a thermal cracking furnace with accouterments for adaptation and switchover from a normally liquid to a normally gaseous feed material. The sequential thermal cracking in this invention is only advantageous when it happens in the sequence of cracking the hydrocarbon having more than two carbon atoms, preferably gasoline or naphtha, first, and then cracking the lower paraffinic hydrocarbon, preferably ethane, second. In a reactor in which ethane is cracked first, followed by cracking of a liquid substrate species, no advantage is realized and even a harmful effect upon the reaction run lengths is noticed.

OBJECTS AND EMBODIMENTS OF THE INVENTION

An object of this invention is to provide a process for the cracking of a lower paraffinic hydrocarbon to a lower olefinic hydrocarbon in a thermal cracking scheme with longer life spans of the thermal cracking reactor.

Another object of this invention resides in a process to acquire ethylene from ethane by cracking the latter to the former in a furnace having a multitude of serpentine situated elongated cracking tubes such that any catalytic effect of the nickel or iron ions on the inside of the reactor tubes is masked thereby preventing unwanted conversion of ethane to coke.

Another object of this invention is a process for acquiring ethylene in a thermal cracking furnace with a precursor hydrocarbon sequentially cracked before charge of the ethane material to selectively form a coat of coke on the tube walls to a thickness of between about 1/16 of an inch and about ⅛ of an inch.

Another object of this invention is to provide a process for the preparation of ethylene via the thermal cracking of ethane in the complete absence of a catalytic composition of matter inclusive of the covered nickel and iron ions of the reactor tube walls and any augmented extrinsic catalyst.

One aspect of this invention concerns an embodiment for a process for the production of ethylene from the pyrolytic cracking of a hydrocarbon consisting essentially of ethane in a pyrolytic cracking furnace having situated therein a plurality of elongated serpentine-situated thermal cracking tubes which comprises: passing a first hydrocarbon feed material having a carbon atom content of $C_3$ and greater through said plurality of elongated serpentine-situated thermal cracking tubes to crack said first hydrocarbon at cracking conditions to produce a first hydrocarbon product and coke, wherein said cracking conditions and throughput of said hydrocarbon is effective to selectively place an amorphous relatively smooth coat of coke on the interior of said plurality of elongated serpentine-situated thermal cracking tubes, wherein said coat of coke is of a thickness of between about 1/16 inch and about ⅛ inch; stopping said passage of said first hydrocarbon feed material through said thermal cracking tubes; and passing a second hydrocarbon consisting essentially of ethane through said plurality of elongated serpentine-situated thermal cracking tubes having said coat of amorphous relatively smooth coat of coke thereon at ethane cracking conditions to crack said ethane to ethylene, which is recovered from said pyrolytic cracking furnace.

Another embodiment of this invention resides in a process for the cracking of a lower paraffinic hydrocarbon to a lower olefinic hydrocarbon by thermal pyrolytic cracking at pyrolytic cracking conditions of said lower paraffinic hydrocarbon at a temperature of about 800° F. to about 1700° F. in a pyrolytic cracking furnace having a plurality of interconnecting elongated serpentine cracking tubes having interior walls, the improvement which comprises precoating said interior walls, before contact of said lower paraffinic hydrocarbon, with an amorphous relatively smooth coat of coke derived from thermal cracking a hydrocarbon having more than two carbon atoms $C_3+$ at a temperature of 800° F. to 1700° F. for a period of time sufficient to form said smooth coat of coke on said tube walls.

Another embodiment of this invention resides in a process for cracking ethane to ethylene in a thermal cracking furnace having a plurality of undulating cracking tubes with interior side walls having nickel, iron or nickel and iron compounds therein which comprises: passing a coke-forming precursor hydrocarbon through said cracking tubes at hydrocarbon cracking conditions including a temperature of 1450° F. to 1600° F., a pressure of 1 bar to 10 bar and a liquid hourly space velocity of 0.2 sec to about 1 sec to selectively and thermally crack said coke-forming precursor hydrocarbon to form at least a layer of coke on the interior sidewalls of said cracking tubes in a depth of from about 1/16 inch to a depth of ⅛ inch and thereby mask at least 90% of said nickel, iron or nickel and iron compounds therein; ceasing flow of said coke-forming precursor hydrocarbon; passing ethane, in the presence of steam, through said cracking tubes at a temperature of 1000° F. to 1600° F., a pressure of 1 bar to 10 bar and a gas hourly space velocity of 0.2 sec to 1.0 sec to crack said ethane to ethylene; passing said produced ethylene to a cooling zone comprising a shell and tube heat exchanger to lower the temperature of said ethylene at least 300° F.; and passing said cooled ethylene to a fractionation zone to separate and purify said ethylene from formed by-products and/or unreacted ethane.

BRIEF DESCRIPTION OF THE INVENTION

Succinctly, this invention resides in a process for the production of ethylene from the pyrolytic cracking of ethane in a pyrolytic cracking furnace wherein a first hydrocarbon feed material having more than two carbon atoms is cracked for a period of time effective to selectively coat the interior walls of reactor tubes situated in the furnace with a smooth amorphous coat of coke to mask any catalytic effect (subsequent cracking of ethane to unwanted coke) of the metals indigenous to the interior walls of the tubes. It has been determined and demonstrated that the run lengths for the pyrolytic cracking tubes are increased on an order of 20 to 50% from the previous selective cracking of a specific hydrocarbon precursor.

DETAILED DESCRIPTION OF THE INVENTION

Since at least the early 1930's many different pyrolysis reactors have been in commercial operation. Generally, some of these reactors are fired tubular heaters for the production of ethylene via the cracking of ethane. As the cracking of ethane to ethylene is highly endothermic, a convection section operates to transfer heat from the radiant section or fire box of the furnace to the tubular heaters. The latter may be in the form of a single row of cracking tubes, or if desired, a multiple row of cracking tubes may be employed. There is no doubt that ethylene can be produced from the pyrolytic cracking of ethane or even higher hydrocarbon feeds such as gasoline, propane or light naphthas. However, as the number of carbon atoms in the feed are increased the relative percent production of ethylene is decreased. It is therefore generally most desirable to formulate ethylene from ethane.

This invention requires a particular sequential cracking of certain hydrocarbons to coat the interior walls of the pyrolysis reactor tubes to mask the catalytic function of catalytic ions indigenous to the cracking tubes which accelerate coke formation and deposition from ethane cracking. The first hydrocarbon cracked in the cracking tubes is a hydrocarbon material, having a carbon number greater than 2, which is again thermally cracked to selectively deposit on the interior surface or walls of the cracking tubes an effective amount of a relatively smooth coat of amorphous coke. If an insufficient amount of coke is placed on the tube walls, coke production from ethane will be catalytically accelerated as a result of the open presence of iron, nickel or both on the interior of the cracking tube walls. However, if too thick a glaze of coke is placed on the interior walls of the cracking tubes, portions of the "masking" coke will break off and cause coke spalling (free floating chunks of coke) analogous to an over abundance of fatty tissues in a blood vessel of a human being. The spalled coke passes through the larger cracking tubes but same will result in a blocking of at least a portion of the tube section of a downstream shell and tube heat exchanger in a manner analogous to the formation of a blood clot in a cardiovascular system of a human being. As the pressure at the inlet of the heat exchanger increases, the rate of coking increases as a result of the increase in hydrocarbon residence time. If the pressure increase were permitted to continue in an exponential manner, the heat exchanger would become blocked to such an extent that regeneration is not possible, i.e. the steam can traverse the exchanger passages. At this point, the exchanger is terminal and must be put out of service. It is preferred that the thickness of the selective coat of coke be no greater than ⅛ of an inch in thickness but no less than 1/16 of an inch in thickness.

The first hydrocarbon feed material is selected from the group consisting of propane, butane, gasoline, naphtha, $C_6+$ hexane raffinate, $C_3$ to $C_7$ hydrocarbon, $C_7$ to $C_{12}$ hydrocarbons and mixtures of same or other highly paraffinic branched hydrocarbons from which $C_2+$ olefins form as a result of their cracking and which are probably the derivative of the relatively smooth form of coke on the vessel walls. Specific examples of such feed streams comprise a propane stream containing up to 10% propylene, a n-butane stream containing up to 90% isobutane, gasoline range streams having initial boiling points of 12° F. and final boiling points of up to 400° F. and naphtha range streams having a boiling range from 100° F. to 600° F. In Table I below four separate distillates are exemplified with the carbon number range shown via their respective boiling points.

TABLE I

| | Raffinate | Light Straight Run Gasoline | Topped Naphtha | Full Range Naphtha |
|---|---|---|---|---|
| True Boiling (by vol %) Point (°F.) | | | | |
| IBP | 12° F. | 24° F. | 121° F. | —° F. |
| 10% | 91 | 96 | 189 | 165 |
| 30% | 135 | 148 | 235 | 234 |
| 50% | 143 | 182 | 271 | 284 |
| 70% | 154 | 198 | 304 | 329 |
| 90% | 193 | 217 | 336 | 383 |
| FBP | 389 | 254 | 684 | 477 |
| TBP Average | 143° F. | 168° F. | 267° F. | 279° F. |
| API gravity | 79.4 | 70.4 | — | 54.7 |
| Specific gravity | .670 | 0.70 | — | 0.760 |
| Molecular weight | 81.9 | — | — | 101 |

It is contemplated within the scope of this invention that the cracking conditions in regard to the first hydrocarbon cracking for the selective formation of the "masking" layer of coke include a temperature of from about 900° F. to 2000° F., a pressure of from about 1 atmosphere to about 100 atmospheres and an hourly space velocity of 0.2 seconds to about 2.0 seconds. While it is preferred that the first hydrocarbon be a liquid at room temperature it is also within the confines of this invention to utilize propane or butane as the first hydrocarbon feed material. It is feasible to crack any $C_3$ and above hydrocarbon to attain the desired precoat coke layer although hydrocarbons boiling below the asphaltene range constitute a preferred upper range of first hydrocarbon feed material. It is of course readily apparent that at the above recited process conditions after preheating, i.e. during cracking, all of these materials are existent in the gaseous phase.

As shown in subsequent FIGS. 2 and 5, the cracking furnace is usually comprised of a large room built of or lined with highly refractory material with a means to admit direct heat via the direct combustion of methane or a fossil fuel. It is also contemplated within the scope of this invention that the furnace be heated by other means, i.e. a coal furnace, or nuclear derived-energy although the same are not within the preferred direct flame embodiment of this invention. In a preliminary heating zone, the feed material is preheated, passed through a conducting tunnel and eventually cracked in a fire box area of the furnace. The hydrocarbonaceous material, whether the first hydrocarbon substrate or the second hydrocarbon (ethane), is confined within a plurality of serpentine-situated cracking tubes which stretch from near the top of the furnace to near the bottom of the furnace in an elongated undulating pattern.

The furnace cracking tubes may be one long interconnected serpentine tube or they may be a pair or more of interconnected tubes situated in the substantial mid-section of the cracking furnace. It is desirable that the hydrocarbonaceous materials pass very rapidly through the serpentine arrangement of heating tubes. For this reason, the same are designed for a throughput of the second hydrocarbon at a specific temperature to insure the cracking of the paraffin (ethane) to the counterpart olefin species (ethylene) while undergoing as little coke production as possible.

The second feed material in this sequential cracking process is a lower paraffinic hydrocarbon including ethane, propane, butane, pentane or hexane. Usually, the preferred species of paraffin is ethane; the corresponding preferred olefin is ethylene. Utilizing the latter as exemplary of this process, ethane is charged in admixture with diluent steam in a ratio of ethane to steam of about 1:0.3 to about 1:0.6. Ethane is cracked at ethane cracking conditions which include a temperature of from about 600° F. to about 2000° F., a pressure of from about 1 atmosphere to about 10 atmospheres (a lower pressure is actually desired) and a gas hourly space velocity of 0.2 to 2 seconds. It is inevitable that the cracking of the ethane will produce non-catalyzed gas phase tars which are then undesirably deposited on the interior sidewalls of the furnace tubes and cooling unit and form coke. However, the amount of coke produced in the gas phase will be a smaller amount of coke over a specific period of time than that produced catalytically in the absence of the select precoat. And the aforementioned selective coating of the interior walls of the furnace cracking tubes via the coke from the first hydrocarbon cracking inhibits the catalytic formation of coke.

The catalytic sites of iron, nickel and other catalytically-active metals are masked by the selective coat of amorphous coke on the interior walls of the furnace cracking tubes. The masking of these catalytic metal sites, which if not covered would catalyze the cracking of at least a portion of the ethane to nefarious coke deposits, is the desired effect of the selective coat of coke formed from the first hydrocarbon feedstock or precursor hydrocarbon coking agent. Thereafter, conversion of ethane pyrolytically to ethylene is made in the near absence of any catalytic composition of matter added either to the feed material or existent as an ion indigenous to the vessel walls of the tubular furnace.

After formation of ethylene, the product effluent is extracted from the cracking tubes in the furnace and passed to a cooling and separation zone. The cooling zone, which quickly cools the ethylene, can be any type of separation and cooling means known to the art. A preferred cooling means comprises a shell and tube type heat exchanger with a multiple number of tubes (as shown in FIG. 4 herein) sufficient for the passage of the hot ethylene effluent in an upward direction in indirect heat exchange with a fluid material, such as boiler feed water, having a temperature less than the temperature of the ethylene effluent. The ethylene effluent is reduced in temperature at least 300° F. and preferably at least 600° F. from the near 1800° F. or 2000° F. temperature existent at emission from the final stage of the tubular thermal cracker. Any other type of fluidized heat exchange media, such as water, freon, alcohols, or other known liquid heat sinks are considered within the confines of this invention but are not necessarily preferred over water for economic or safety reasons. The reduction in temperature of the ethylene will ensure that no further conversion or cracking occurs to form coke or other less desirable hydrocarbons.

Downstream of the cooling zone, the cooled reaction product is passed through a series of fractionation units for further reduction in temperature and fractionation of the ethylene to a pure state. It is conceivable that some impurities in the ethane will be present in the ethylene and will necessitate further fractionation. Any recovery of uncracked ethane or paraffinic by-product can be recycled to the cracking zone, with or without a purification procedure to guard against the unwanted accumulation of impurities in the cracking tubes.

DETAILED DESCRIPTION OF THE DRAWINGS

Figure 2:
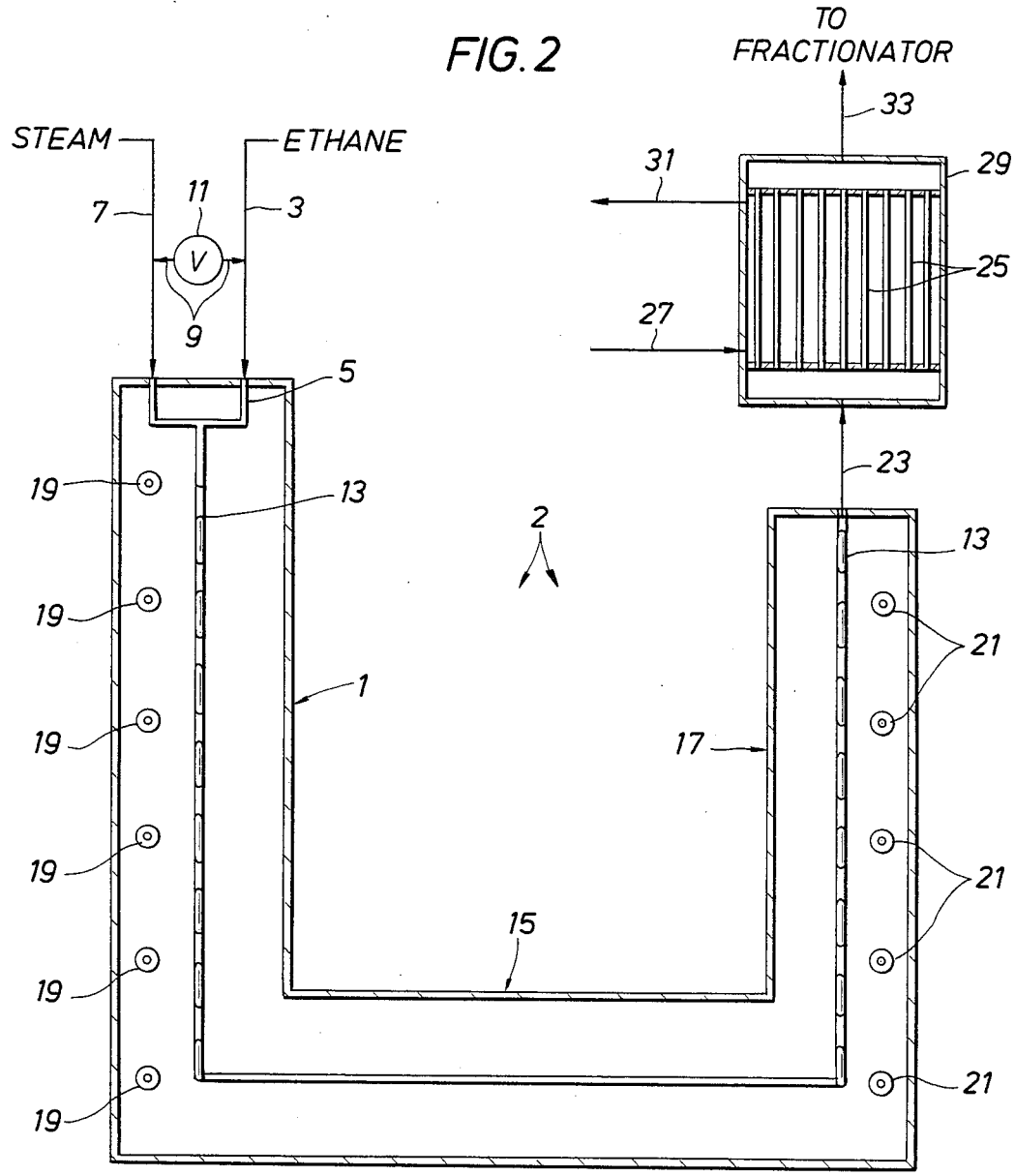
FIG. 2 is an overview of the instant process beginning with the feed material and ending with the cooled ethylene product being passed to downstream fractionation separation.

Ethane is shown in FIG. 2 as an exemplary paraffinic material to be cracked to ethylene in the presence of diluent steam. Ethane is charged to a pre-heating section 1 of furnace 2 through conduit 3 and inlet manifold 5. Steam is admixed through conduit 7 and manifold 5 with the ethane. Either of these components may be pre-mixed before charge to manifold 5 utilizing conduit 9 and movable valve 11. Manifold 5 is in communication with tubular cracking reactor units 13 constructed for passage through the furnace comprising preheat zone 1, tunnel 15 and fire box 17. A plurality of direct fired burners 19 are situated in the preheat section of the furnace as an optional means to preheat the ethane feed. If desired, direct heaters 21, which are necessary to maintain endothermic pyrolytic cracking conditions in the fire box, can be used to preheat the ethane feed in conduit 13 (even in preheat section 1) and thereby vitiate installation of direct fired heaters 19. Ethane flows very rapidly through tubes 13 in preheat section, 1 through tunnel area 15 and to fire box 17. It is conceivable (but not necessarily desired) within the scope of this invention that preheat section 13 and tunnel section 15 can be emasculated to eliminate overall capital cost as long as some type of preheat means is provided for the ethane's heated traversal to fire box 17. It is also contemplated that fire box unit 17 may be segmented into more than one area (and preferably three areas) to more fully utilize the designed temperature profiles for ethane cracking.

The temperature at the bottom of the tubes can be as low as 600° F. while the temperature in the top of the tubes can be as high as 2000° F. For this reason, the constant cooling and heating of the ethane during traversal of the tubular cracking reactors creates a considerable strain on the metallurgy of same, which may cause the tubes to bend or bow so as to be situated not necessarily in a straight linear up and down relationship with one another. Ethane is cracked to ethylene in tubes 13. Ethylene egresses from fire box unit 17 in pyrolytic cracking tubes 13 via conduit 23 and is passed, utilizing a head manifold not shown in the instant drawing, to a multitude of tube sections 25 for passage in an upward direction to the top of heat exchanger 29. A heat exchange fluid, such as water or steam, is augmented to the shell side of the shell and tube heat exchanger 29 by ingress means 27 and egress means 31. The temperature of ethylene in conduit 23 is much higher than the temperature of the ethylene in a cooling zone (heat exchanger) effluent 33; the temperature of the fluid in conduit 31 is much higher than the temperature of the fluid in conduit 27.

Figure 4:
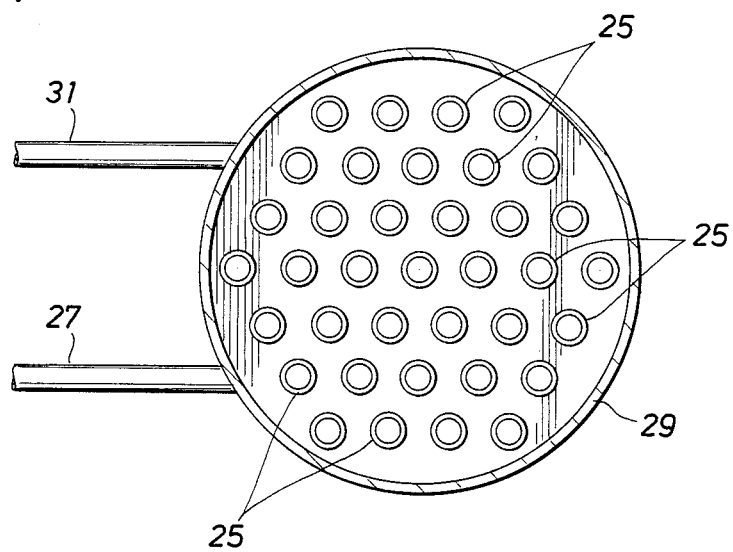
FIG. 4 is a cross-section view of a downstream shell and tube heat exchanger for cooling the ethylene product from the cracking tubes.

FIG. 4 shows a cross section view of the heat exchanger or cooling zone 29 having a multitude of tube sections 25. These sections may be sporadically placed in the heat exchanger or preferably they may be placed at an intermittent distance with respect to one another so as to maximize the cooling effect of the cooler heat exchange fluid. It should be noted that the openings in these tubular structures are usually the first victims of the ethane coking phenomena i.e. coke spalling and may require the shutdown of the ethane cracking furnace even though the tubes used for pyrolysis of the ethane in the fire box unit are still relatively clear of ethane-formed coke. For example, if too thick a coke layer is deposited by the first hydrocarbon cracking step, the spalled carbon particles will usually become lodged at the bottom of tubes 25 thereby blocking the flow of the ethylene product therethrough and of course thereby diminishing greatly the capacity of heat exchanger unit 29 to cool the ethylene product.

Figure 5:
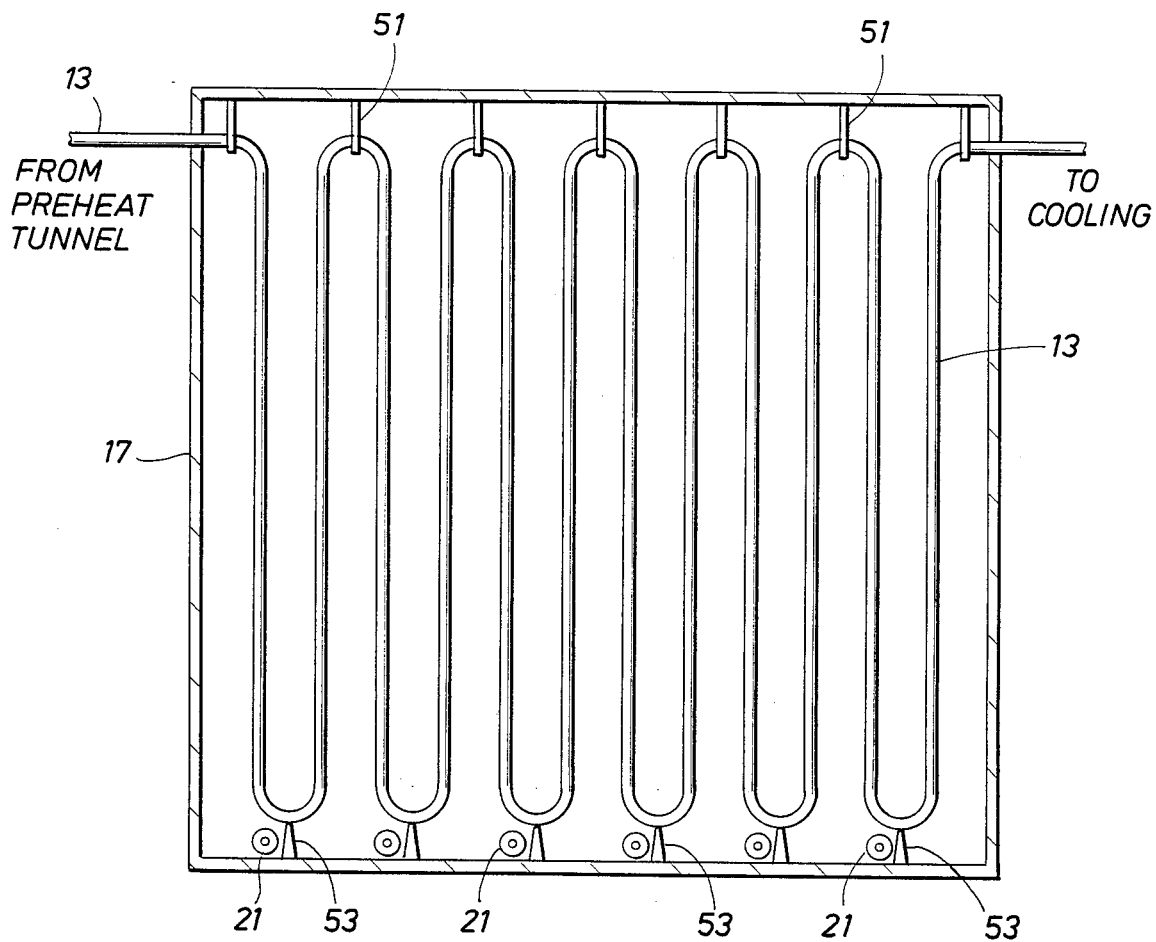
FIG. 5 is a side elevation view of the fire box of the instant furnace having elongated serpentine or undulating tubular cracking reactors.

FIG. 5 is a side view of fire box 17 having serpentine or undulating pyrolytic tubes 13 for cracking of the ethane therein. These tubes are preferably suspended from the ceiling by leveling hanger means 51 and rest on support means 53 placed in a special relationship vis-a-vis burners 21.

Figure 3A:
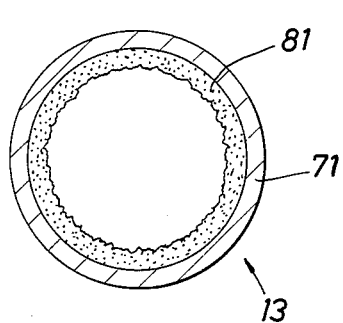
FIG. 3A is a cross-section view of a pyrolytic cracking tube after a complete ethane run has been completed with an unsuitable amount of coke deposited on the interior walls of the cracking tube.
Figure 3B:
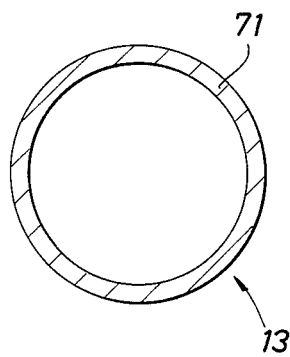
FIG. 3B shows a cross-section view of a pyrolytic cracking tube at a time immediately preceding the introduction of ethane and subsequent to the ceasing of the first hydrocarbon cracking.

FIGS. 3A and 3B show a cross section of the furnace tubes both before (3B) and after (3A) ethane coking. FIG. 3A shows the select formation of the amorphous relatively smooth coat of coke 71 having deposited thereon ethane formed coke 81 which causes the "hardening of the arteries" of the tubular reactors and downstream cooling unit eventually causing premature shutdown of same. It is coke layer 81 that applicants seek to mitigate or at least put off in time-of-formation by use of selective coating of coke layer 71. FIG. 3B shows layer 71 which, if possible, encompasses at least 90% of the surface area of the internal walls of the coking oven and has a thickness of no greater than ⅛ of an inch and no less than 1/16 of an inch of amorphous relatively smooth coke. FIG. 3B therefore shows a cross-section view of the tubular reactor at a time immediately before the initiation of ethane coking and immediately subsequent to the laying down of the pre-select layer of greater than $C_2$ hydrocarbon-formed coke. It should also be noted, although not shown in the drawings, that a sample of coke from either the tubular furnaces or the downstream cooling section have different visual substrates in regards to the coke formed by these two sequential hydrocarbon processes. For instance, one is a shiny black substrate representative of the coke formed derivative of the greater than $C_2$ hydrocarbon cracking while ethane derived coke is very porous and brittle.

EXAMPLES

The instant examples are given to exemplify the unexpected increase in run lengths attained via the select precoating of the coke derivative of the greater than $C_2$ hydrocarbon cracking before admission of ethane. Applicants are providing these examples as an exemplary of the surprising results determined in the actual operation of a cracking furnace modified to accommodate both liquid and gaseous feed materials and are not provided as a limitation upon the claims of this invention.

EXAMPLE 1

Figure 1:
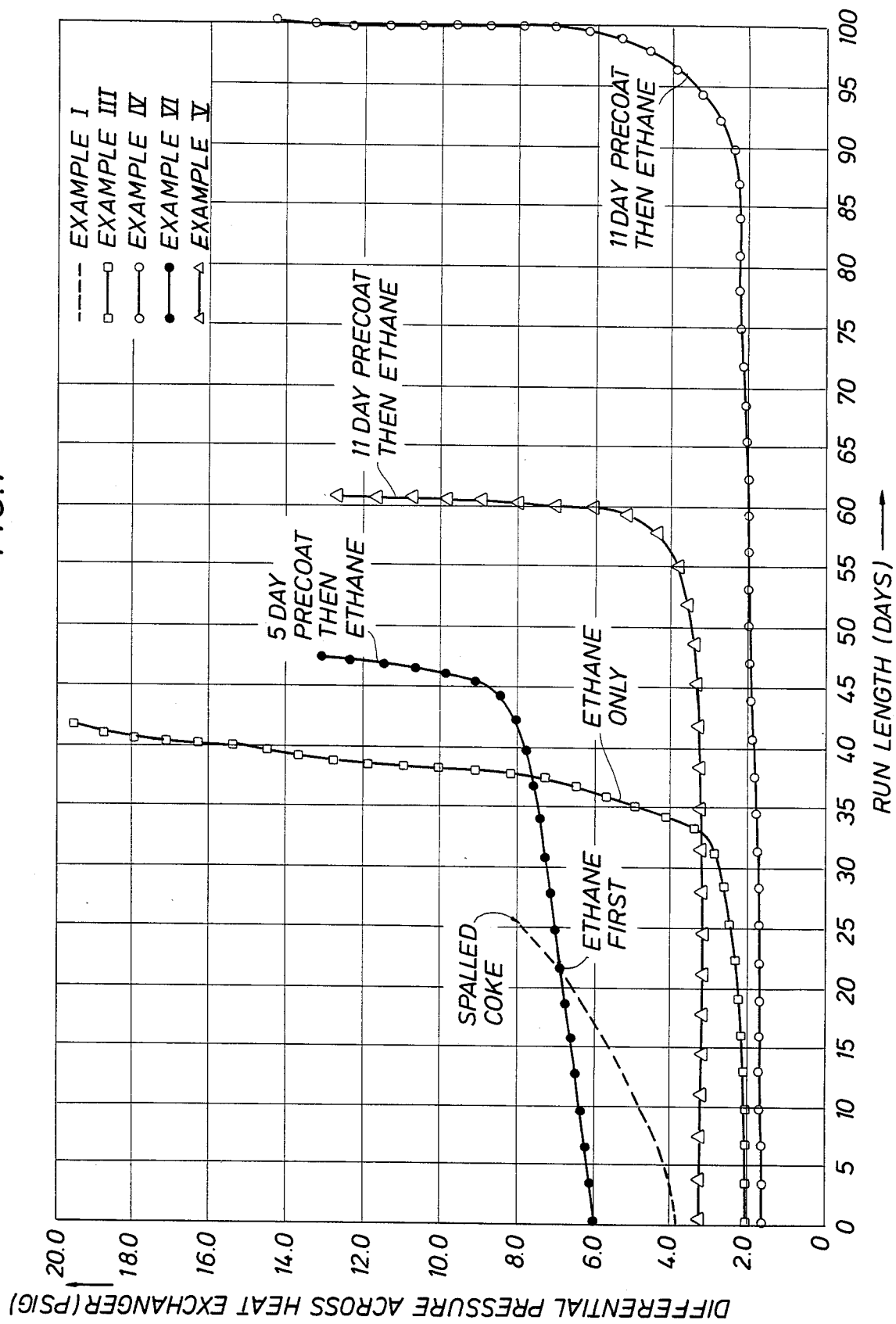
FIG. 1 shows a graphic comparison of furnace tube run length in days for the experiments conducted with ethane cracking first followed by liquids, only ethane cracking and ethane cracking preceded by a selective cracking process to coat the furnace tubes with an amorphous relatively smooth coke coat.

In this example, the sequential hydrocracking system was reversed in that ethane was cracked first to deposit a ethane-coke derived layer on the cracking walls before introduction of a liquid feed having a gasoline range boiling point. Ethane was added into the preheat section of the furnace at a temperature of 240° F., exited the preheat section at 1100°–1190° F., and traversed into the fire box section maintained at a temperature of about 2050° F. The ethane was continuously cracked for a period of 25 days continuous run length at which time it was assumed that a layer of the ethane coke was deposited on the cracking furnace walls and in the downstream heat exchanger. Thereafter, a liquid feed comprising a gasoline boiling range material was added to the cracking furnace after the passage of ethane was ceased. Immediately the ethane-derived coke began spalling and immediately plugged the tubes of the downstream heat exchanger. The run length was 25 total days for the ethane and less than 1 day for the liquid feed material. This is shown in FIG. 1 and Table II.

EXAMPLE 2

In this example, again ethane was cracked first followed by cracking of a vapor catalytic cracked dry gas containing vaporized $C_5/C_6$ fractions second. The total ethane run length was again 26 days and the pressure immediately jumped in the downstream heat exchanger after initiation of cracking the second hydrocarbon. It was determined that the immediate rise in downstream heat exchanger pressure defeated any purpose in continuing the cracking of the second feed.

EXAMPLE 3

In this example only ethane was cracked to ethylene without any other feed material. The pressure in the heat exchanger reached an unmanageable level after 35 total run length days demonstrating the total run length which can be obtained without pre-select coating of the cracking tubes.

EXAMPLES 4 THROUGH 7

These experiments demonstrate the pre-select coating of the cracking tubes of this invention. In runs 4 and 5 a liquid gasoline feed was run for 11 days at 1480°–1500° F. coil outlet to selectively place a layer of coke having a depth believed to be between ⅛ inch and 1/16 inch of relatively smooth amorphous coke on the furnace tube walls. After this cracking, ethane was charged and the reactor allowed to run until the pressure in the heat exchanger outlet became intolerable.

Test runs 6 and 7 utilized a liquid hydrocarbon cracking step first over a period of time insufficient to form the necessary layer of coke in the tubes. The run lengths of ethane lasted respectively 48 and 35 days.

The results of these examples are summarized in Table II.

TABLE II

| Example | Feed | Heat Exchange Pressure[1] SOR | EOR | °F. | Total Ethane Run Length |
|---|---|---|---|---|---|
| 1 | Ethane first Liquid hydrocarbon second | Spalled coke-immediate blockage | | | 25 days |
| 2 | Ethane first FCC[2] gas second | 16.0 | 25.6 | | 26 days |
| 3 | Ethane only | 16.2 | 30.8 | | 35 days |
| 4 | 11 days of gasoline feed then ethane | 14.2 | 25.6 | | 101 days |
| 5 | 11 days of gasoline feed then ethane | 16.5 | 21.9 | | 58 days |
| 6 | 5 days of gasoline feed then ethane | 17.8 | 24.0 | | 48 days |
| 7 | 8 days of gasoline feed then ethane | 15.4 | 23.4 | | 35 days |
| 8 | 4 days of gasoline feed then | 17.2 | 28.2 | | 21 days |

TABLE II-continued

| Example | Feed | Heat Exchange Pressure[1] SOR | EOR | °F. | Total Ethane Run Length |
|---|---|---|---|---|---|
| 9 | 5 days of gasoline feed then ethane | — | 23.0 | | 20 days |

[1]SOR indicates pressure at start of run.
EOR indicates pressure at end of run.
[2]FCC gas is the off-gas of a fluid-bed catalytic cracking unit. It contains up to 10% wt. $C_5/C_6$ material.

It can clearly be seen that a certain amount of coke derived from a liquid hydrocarbon feed must be placed on the interior walls of the tube furnaces to obtain the much greater run lengths of the ethane feed as shown in Example 4. The exact duration of these run lengths can vary depending on the conditions and the particular hydrocarbon feed which is to be first cracked. The run length of the first precoat step must be sufficient to place the greater than $C_2$ hydrocarbon cracked coke to a depth of greater than 1/16 of an inch but less than 1/18 of an inch.

The end of the cracking furnace run length is indicated by the pressure at the inlet of the heat exchanger referred to as end of run (EOR). This exact pressure may vary for different cracking runs but once this pressure begins to climb into the lower 20's, a point is reached where the pressure, through continued operation, rises drastically in an exponential manner. Note the rapid rise in the pressure denoted by the ordinate in FIG. 1.

What we claim as our invention:

1. A process for the production of ethylene from the pyrolytic cracking of a hydrocarbon consisting essentially of ethane in a pyrolytic cracking furnace having disposed therein a plurality of elongated serpentine-situated thermal cracking tubes which comprises:
   (a) passing a first hydrocarbon feed material having a carbon atom content of greater than 2 through said plurality of elongated serpentine-situated thermal cracking tubes to crack said first hydrocarbon at cracking conditions effective to produce a first hydrocarbon product and coke, wherein said cracking conditions and throughput of said first hydrocarbon is sufficient to selectively place an amorphous relatively smooth coat of coke on the interior of said plurality of elongated serpentine-situated thermal cracking tubes, wherein said coat of coke is of thickness of about between about 1/16 inch and about ⅛ inch;
   (b) stopping said passage of said first hydrocarbon feed material through said thermal cracking tubes; and
   (c) passing a second hydrocarbon consisting essentially of said ethane through said plurality of elongated serpentine-situated thermal cracking tubes having said coat of amorphous relatively smooth coat of coke thereon at ethane cracking conditions to crack said ethane to ethylene, which is recovered from said pyrolytic cracking furnace.

2. The process of claim 1 further characterized in that said first hydrocarbon is a naphtha range boiling hydrocarbon.

3. The process of claim 1 further characterized in that said first hydrocarbon is a gasoline range boiling hydrocarbon.

4. The process of claim 1 further characterized in that said first hydrocarbon is propane or butane or mixtures of propane and butane.

5. The process of claim 1 further characterized in that said cracking conditions include a temperature of from 800° F. to 2000° F., a pressure of from 1 atmosphere to 100 atmospheres and a hourly space velocity of 0.2 sec to about 2.0 sec.

6. The process of claim 1 further characterized in that said ethane cracking conditions include a temperature of from about 600° F. to about 2000° F., a pressure of from about 1 atmosphere to about 10 atmospheres and a gas hourly space velocity of 0.2 to 2.0 secs.

7. The process of claim 1 further characterized in that said coat of amorphous relatively smooth coke functions to cover a predominated number of catalytic metal sites on the interior walls of said tubes.

8. The process of claim 7 further characterized in that said catalytic metal sites include the ions of iron and nickel.

9. The process of claim 8 further characterized in that said iron and/or nickel metal sites are sufficient, if not covered, to catalyze the cracking of at least a portion of said ethane to a filamentous coke deposit.

10. The process of claim 1 further characterized in that said ethane is cracked to ethylene in the near absence of catalytic metals sites on the interior of the tube walls as a result of said coat of amorphous relatively smooth coat of coke.

11. The process of claim 1 further characterized in that said ethylene produced in step (c) is removed from said pyrolytic cracking furnace and is passed to a cooling zone wherein the temperature of said ethylene is reduced to a temperature of about 900° F. or lower.

12. The process of claim 1 further characterized in that said second hydrocarbon consisting essentially of ethane is admixed with diluent steam in a ratio of ethane to steam of about 1:0.3 to about 1:0.6.

13. The process of claim 11 further characterized in that said cooling zone is a shell and tube heat exchanger with boiler feed water in said shell side of said heat exchanger at a temperature of about 530° F. to about 600° F. and with said ethylene product in said tube side of said heat exchanger.

14. The process of claim 1 further characterized in that said pyrolytic run length exceeds 20 to 50 percent of its normal run life as a result of said coat of amorphous relatively smooth coke.

15. In a process for the cracking of a lower paraffinic hydrocarbon to a lower olefinic hydrocarbon by thermal pyrolytic cracking at pyrolytic cracking conditions of said lower paraffinic hydrocarbon at a temperature of about 800° F. to about 1700° F. in a pyrolytic cracking furnace having a plurality of interconnecting elongated serpentine cracking tubes having interior walls, the improvement which comprises precoating said interior walls, before contact of said lower paraffinic hydrocarbon, with an amorphous relatively smooth coat of coke derived from hydrocracking a hydrocarbon having more than two carbon atoms at a temperature of 800° F. to 1700° F. for a period of time sufficient to form said smooth coat of coke on said tube walls.

16. The process of claim 15 wherein said lower paraffinic hydrocarbon is ethane and said produced lower olefinic hydrocarbon is ethylene.

17. The process of claim 15 wherein said hydrocarbon having more than two carbon atoms is selected from the group consisting of propane, butane, gasoline boiling hydrocarbons, naphtha boiling hydrocarbons, and $C_6$–$C_{12}$ paraffin hydrocarbons.

18. The process of claim 15 wherein said thermal pyrolytic cracking of said lower paraffinic hydrocarbon is performed in the absence of an added catalyst.

19. The process of claim 15 wherein said lower paraffin hydrocarbon is thermally cracked in a cracking furnace comprising a plurality of elongated serpentine steel tubes having interior sidewalls.

20. The process of claim 15 wherein said interior sidewalls of said tubes possesses active nickel, iron, nickel and iron or other combinations of catalytic metal sites.

21. The process of claim 15 wherein said nickel, iron or nickel and iron sites, or other metals are catalytically active to catalyze the conversion of ethane, by pyrolytic cracking, to coke having a filamentous configuration.

22. The process of claim 21 wherein said nickel, iron, nickel and iron, or other metal sites are selectively masked by deposition of said amorphous relatively smooth coat of coke derived from thermal cracking of said hydrocarbon having more than two carbon atoms.

23. The process of claim 15 wherein said pyrolytic cracking is performed in a plurality of serpentine-situated steel tubes downstream of a lower paraffinic hydrocarbon preheating zone.

24. The process of claim 16 wherein said ethylene product is removed from said pyrolytic cracking and passed to a cooling zone wherein said ethylene is cooled to at least a temperature differential of 300° F. in comparison with the temperature of said ethylene egressing from said pyrolytic cracking.

25. The process of claim 24 wherein said cooling zone comprises a shell and tube type heat exchanger having said ethylene product in said tube side and boiler feed water in said shell side of said heat exchanger, wherein the temperature of said ethylene is reduced by transferring indirectly the latent heat of said ethylene to said boiler feed water which undergoes a temperature increase during passage through said shell and tube type heat exchanger.

26. The process of claim 25 wherein said cooled ethylene exiting said shell and tube type heat exchanger is passed to a fractionation zone for excising of said ethylene from any pyrolytically formed by-products or unconverted ethane.

27. The process of claim 15 wherein said hydrocracking of said hydrocarbon having more than two carbon atoms is perfomed at a temperature of 900° F. to about 1700° F., a pressure of about ambient to about 10 atmospheres and a liquid hourly space velocity of about 0.2 to about 1 sec in the presence of hydrogen.

28. The process of claim 15 wherein said pyrolytic cracking conditions include a temperature of 900° F. to about 1700° F., a gas hourly space velocity of about 0.2 sec to about 1.0 sec and a pressure of about 0.5 atmospheres to about 4 atmospheres.

29. The process of claim 19 wherein said amorphous relatively smooth coat of coke is sufficient to coat at least 90% of said interior walls of said steel tubes.

30. A process for cracking ethane to ethylene in a thermal cracking furnace having a plurality of undulating cracking tubes with interior sidewalls having nickel, iron, nickel and iron, or other metal compounds therein which comprises:
  (a) passing a coke-forming precursor hydrocarbon through said cracking tubes at hydrocarbon cracking conditions including of a temperature of 1300° F. to 1600° F., a pressure of 1.0 bars to 10 bars and a liquid hourly space velocity of 0.2 to about 1.0 sec to selectively and thermally crack said coke-forming precursor hydrocarbons to form a layer of coke on the interior sidewalls of said cracking tubes in a depth of from about 1/16 inch to a depth of ⅛ inch and thereby mask at least 90% of said nickel, iron, nickel and iron, or other metal compounds therein;
  (b) ceasing flow of said coke-forming precursor hydrocarbon;
  (c) passing ethane, in the presence of steam, through said cracking tubes at a temperature of 900° F. to 1600° F., a pressure of 1.0 bar to 10 bar and a gas hourly space velocity of 0.2 to 1.0 to crack said ethane to ethylene;
  (d) passing said ethylene from step (c) to a cooling zone comprising a shell and tube heat exchanger to lower the temperature of said ethylene at least 300° F.; and
  (e) passing said cooled ethylene to a fractionation zone to separate and purify said ethylene from by-products formed in step (c) or unreacted ethane.

31. The process of claim 30 wherein steam is present in a ratio based on the ethane of 0.3:1 to 0.6:1.

32. The process of claim 31 wherein said layer of coke on the interior sidewalls of said cracking tubes masks said nickel, iron, iron and nickel, or other catalytic metal sites to the extent that 20% to 50% additional ethane is passed through said furnace before a time is reached where ethane-formed coke deposits on the interior walls of the cracking tubes prevents further ethane cracking therein.

33. The process of claim 31 wherein said coke-forming precursor compounds are $C_3$ to $C_{12}$ hydrocarbons having saturated bonding.

34. The process of claim 33 wherein said $C_3$ to $C_{12}$ hydrocarbons comprise a mixture of $C_5$ saturated hydrocarbons.

35. The process of claim 33 wherein said $C_3$ to $C_{12}$ hydrocarbons comprise a mixture of $C_5$ to $C_{12}$ saturated hydrocarbons.

36. The process of claim 33 wherein said $C_3$ to $C_{12}$ hydrocarbons comprise a mixture of propane and butane.

37. The process of claim 1 wherein said first hydrocarbon is a hydrocarbon having from 7 to 12 carbon atoms.

* * * * *